United States Patent [19]
Murley

[11] Patent Number: 5,244,666
[45] Date of Patent: Sep. 14, 1993

[54] PRESURGICAL SKIN SCRUB AND DISINFECTANT

[75] Inventor: Jack C. Murley, O'Fallon, Ill.

[73] Assignee: Consolidated Chemical, Inc., St. Louis, Mo.

[21] Appl. No.: 830,643

[22] Filed: Feb. 4, 1992

[51] Int. Cl.$^5$ .................. A01N 25/00; A61K 31/74; C11D 9/50; C11D 15/00

[52] U.S. Cl. .................. 424/405; 424/78.07; 424/78.25; 424/719; 252/107; 252/108; 252/110; 252/32

[58] Field of Search ............... 514/244, 560, 642, 643; 424/405, 78.07, 78.25, 719; 252/107, 108, 110, 32

[56] References Cited
U.S. PATENT DOCUMENTS

| | | | |
|---|---|---|---|
| 4,022,911 | 5/1977 | Goldhaft et al. | 514/643 |
| 4,125,628 | 11/1978 | Goldhaft et al. | 514/643 |
| 4,134,971 | 1/1979 | Inoue et al. | 514/527 |
| 4,290,846 | 9/1981 | Muntwyler | 514/737 |
| 4,321,257 | 3/1982 | Sipos | 424/78.06 |
| 4,486,405 | 12/1984 | Klein | 514/845 |
| 4,900,721 | 2/1990 | Bansemir et al. | 514/901 |
| 4,990,329 | 2/1991 | Sampathkumar | 514/900 |
| 5,017,617 | 5/1991 | Kihara et al. | 514/635 |
| 5,122,541 | 6/1992 | Eggensperger et al. | 514/724 |

Primary Examiner—Nathan M. Nutter
Attorney, Agent, or Firm—Paul M. Denk

[57] ABSTRACT

A preoperative surgical skin scrub and wound disinfectant is provided wherein a quaternary ammonium compound and substituted phenolic compound are combined for enhanced microbial activity along with skin conditioners, detergents, emulsifiers, foaming agents, stabilizers and wetting agents to produce a product with enhanced microbial action cleaning and degreasing properties as well as being non-irritating.

14 Claims, No Drawings

PRESURGICAL SKIN SCRUB AND DISINFECTANT

BACKGROUND OF THE INVENTION

This invention relates to surgical scrubs and wound disinfectants more particularly to a surgical scrub and wound disinfectant that has enhanced antimicrobial activity, cleansing and degreasing properties, as well as being gentle and soothing to the skin.

Surgical scrubs are well known in the art. Surgical scrubs are used to prepare the patient's skin before a surgical or operative procedure. The surgical scrub is used to mechanically cleanse the area of the skin to be cut by the surgeon's scalpel, to degrease the skin, remove perspiration and dead skin cells, and to kill bacteria found on the skin. Antibacterial activity is necessary so that the surgeon's scalpel does not introduce bacteria into the incision and promote wound infection. Surgical scrubs are used to kill microorganisms on the skin, particularly, staphylococcus aureus, methicillen-resistant staphylococcus aureus, escherichia coli, pseudomonas aeruginosa and candida albicans. An ideal skin scrub has detergents for cleaning along with detergent emulsifiers for degreasing the skin as well as antimicrobial agents that kill bacteria instantly upon contact.

Two examples of pre-operative skin care products or scrubs well known in the art are Betadine, which has the active antimicrobial ingredient povidone iodine and Hibiclens which incorporates the active microbial agent chlorhexidine gluconate. There are a number of "generic" products available to users that incorporate the same active ingredients as the aforementioned examples. However, povidone iodine can stain the skin, bed linens, and user's hands. Neither povidone iodine nor chlorhexidine gluconate are suited to use on an open wound or pour onto a laceration or abrasion. Benzalkonium, a quaternary ammonium disinfectant consisting of a mixture of alkyldimethylbenzyl ammonium chlorides, is used as a germicide for instruments, etc., but is poorly suited for human skin. It is used as an antiseptic for skin preoperatively in veterinary cases, but is not suited for a surgical scrub because it is incompatible with anionic detergents, such as soap, which are needed to cleanse and degrease the perioperative area.

Various other prior art patents that relate to the subject matter of this invention, pertaining to a form of surgical scrub composition or instrument, include the U.S. Pat. No. 3,063,895, entitled "Disinfectant Compositions," and which defines an improvement in a disinfectant composition. As can be seen, it contains a phenol, an alcohol, ammonium salts, and a chlorphenol, embodied in an aqueous solution, to function as a disinfectant for destruction of bacteria, fungi, and fungal and bacterial spores.

The patent to Irani, et al, U.S. Pat. No. 3,671,644, describes an antiseptic composition which does contain a phenolic or quaternary ammonia, functioning as a bacteriacide, and which is applied to sanitizing compositions, antiseptic detergent compositions, cosmetic compositions, and the like.

The patent to Goldhaft, et al, U.S. Pat. No. 4,125,628, also discloses a disinfectant composition made up of quaternary ammonia, a phenol or derivative thereof, and formaldehyde. It is used to fight bacteria, and has its most effective usage in the treatment of poultry and animal husbandry.

The patent to Mayhew, et al, U.S. Pat. No. 4,209,449, defines a phosphate quaternary compound. It has the formula as shown in the abstract, and it can be seen from its column 3 of the patent that it is compatible with human tissue, etc., and apparently can be used with only slight irritation when applied during medical treatment. The patent also defines its composition can be used in shampoos, or the like. But, it appears that this particular compound is more phosphate based, in its formulation.

The patent to Selega, et al, U.S. Pat. No. 4,237,112, defines a medicated hair and scalp condition. Its ingredients include a petrolatum, a mineral wax, a polyoxy-ethylene, and sulfur. It is primarily used as hair and scalp conditioning composition.

The patent to Sipos, U.S. Pat. No. 4,321,257, discloses a potentiated medicament. It is an antimicrobial composition, incorporating quaternary ammonia compounds, antifungal agents, phenols, and a variety of antiseptics, antibiotics, and the like. It is used as a surgical scrub solution, and foruse as a topical wound dressing, particularly where the presence of blood and wound exist. More specifically, the patent describes that it is a antimicrobial composition, which incorporates a cyclohexyl phneol, having a particular structure, containing a total number of carbon atoms within its alkyl group, wherein the antimicrobial agent is a member selected from a particular group of antibiotics, etc., including quaternary ammonia compounds, as defined.

The patent to Mayhew, et al, U.S. Pat. No. 4,336,385, defines a phosphate imidazolinium compound. It is for use for a variety of purposes, including in shampoos. It composition defines a phosphate quatenary compound having a very distinct formula, including phosphate, chloride, incorporating various alkyl groups of seven to seventeen carbon atoms, within its composition.

The patent to Columbus, et al, U.S. Pat. No. 5,015,228, does disclose a sterilization dressing device and method for skin puncture. This dressing device includes a cover sheet and a gel medium attached to the cover sheet, having a sterilizing agent therein, and for use for apparently disinfecting the portion of the skin being analyzed, and to maintain sterility, when a biopsy needle, or the like, is applied.

The patent to Bansemir, et al, U.S. Pat. No. 5,030,659, discloses another type of disinfectant composition. It is a liquid material, for use as a disinfectant, having at least one microbicidial quatenary ammonium compound, a biguanide compound, and at least one microbicidal phenolic compound. It is in liquid form, and is used for disinfectant purposes. It also states, though, that its compound can be used for surface disinfectant in hospitals, schools, public baths, public transport, and in commercial establishments such as hotels and laundries.

The U.S. Pat. No. 4,022,911, to Goldhaft, et al, is similar to the disinfectant composition as previously patented by these inventors, as earlier explained in U. S. Pat. No. 4,125,628. It is a disinfectant composition, containing quaternary ammonia, phenol and formaldehyde.

Canadian patent No. 1,132,990, defines a process for preparation of phosphorous containing surface active agents. It is a phosphorous-containing reactant, containing an amine, for producing certain phosphobetain compounds.

In summary, the antimicrobial compounds known to the art, but not necessarily combined with skin soothing ingredients, detergents or emulsifiers to produce and acceptable surgical scrub, include, as previously detailed, the U.S. Pat. No. 4,022,911 to Goldhaft, et al, which discloses a disinfectant composition comprising a dimethyl quaternary ammonium halogen salt a phenol, and formaldehyde for use in the poultry and animal husbandry fields. U.S. Pat. No. 3,063,895 to Pearson, et al. discloses multiple phenolic compounds; and U.S. Pat. No. 3,671,644 to Irani, et al. discloses an antiseptic composition containing phenolic antimicrobials potentiated with phosphonic acid derivatives.

None of the above examples teaches a combination of the claimed antimicrobial agents (i.e. a quaternary ammonium compound and substituted phenol) and degreasing emulsifiers and detergents as well as skin softeners and soothing agents. More importantly, the present invention is novel in the use of a compatible quaternary ammonium compound with a substituted phenolic compound such as chloroxylenol or parachlormetaxylenol to obtain enhanced antimicrobial action at lower chemical concentrations.

BRIEF SUMMARY OF THE INVENTION

It is therefore, an object of the present invention to combine a quaternary ammonium compound with a substituted phenolic compound to achieve enhanced broad spectrum antimicrobial action at lower chemical concentrations.

Another object of the invention is to provide a disinfectant for skin that can be used as a surgical scrub or can be used on open wounds such as lacerations or abrasions.

Still another object of the invention is to combine the antimicrobial agents with emulsifiers and detergents to both disinfect and clean and degrease the skin.

Still another object of the invention is to provide a surgical scrub that eliminates over 99% of the targeted bacterial organisms on the skin in 30 seconds of contact time.

Another object of the present invention is to provide a surgical scrub that is gentle and eliminates dermal irritation and is non-staining, and is pleasant to use.

A further object of the invention is to provide a surgical scrub that is practically non-toxic and conforms with the Federal Hazardous Substances Act.

A still further object of the invention is to provide a cost effective, convenient infection control product that is pleasant to use, convenient, easy to package and store.

Other objects of the invention will be obvious to those skilled in the art upon reading the description of the invention.

DESCRIPTION OF THE INVENTION

The present invention relates to a liquid preparation used as a presurgical skin scrub or wound disinfectant containing an antimicrobial quaternary ammonium compound combined with and enhanced by a substituted phenolic compound. The antimicrobial agents are placed in a aqueous vehicle containing emulsifiers detergents, foaming agents, stabilizers and other ingredients.

The present invention contains a combination of the following material as expressed in approximate percentages weight/weight:

(a) At least one quaternary ammonium compound, about 3%
(b) At least one substituted phenolic compound, about 3%.
(c) water, about 55%
(d) citric acid, about 0.14%
(e) cocamidopropyl betaine, a viscosity builder and emulsifier, about 3%
(f) EDTA (ethylendiamine tetraacetic acid) a stabilizer, about 0.05%
(g) sodium lauryl sulfate, a detergent, about 22%
(h) cocamide DEA a viscosity builder, about 8%
(i) propylene glycol, a suspending agent, about 5%
(j) aloe vera, an emollient, about 0.12%
(k) hydrolyzed collagen, a healant, about 0.12%
(l) fragrance, and
(m) a coloring agent.

The process for making the invention is as follows:
Heat about ⅔ of the total water to about 190° F. and maintain. Add to the water the following ingredients mixed in order:
citric acid,
cocamidopropyl betaine
quaternary ammonium compound
EDTA
sodium lauryl sulfate
cocamide DEA.,
Mix the following ingredients in order and add to the above mixture:
propylene glycol,
substituted phenolic compound.
Mix the above combinations together until a uniform mixture; cool to about 120° F. and add:
aloe vera gel,
hydrolyzed collagen
fragrance
and coloring agent.
Add the additional final ⅓ (approx.) of the water.

The product is an aqueous solution of the aforementioned materials having a pH approximately 5.0–8.0 and a specific gravity of 0.5–1.5.

All numbers that express quantities of ingredients or conditions or temperatures used herein are understood as modified in all instances by the term about.

Particularly suitable quaternary ammonium compounds are phosphate quaternary compounds of the general formula:

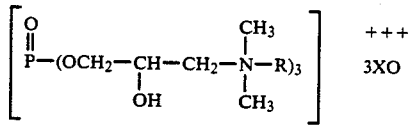

wherein R is a tertiary amine radical of from 6 to 40 carbon atoms; and X is an anion as disclosed in U.S. Pat. No. 4,209,449 to Mayhew, et al. or phosphate imidazolinium compounds, having the general formula:

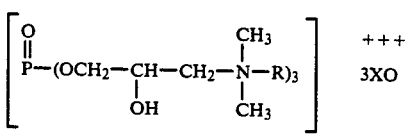

wherein R is a tertiary amine radical of from 6 to 40 carbon atoms; and X is an anion, as described in U.S. Pat. No. 4,336,385, to Mayhew, et al.

The present invention demonstrates the following antimicrobial activity in the percent Bacterial Reduction Test (NCCLS Document M26-Protocol).

| Percent Bacterial Reduction | | |
| --- | --- | --- |
| Organisms Used | Contact Time | % Reduction |
| *Staphylococcus aureus* | 30 seconds | 99.99% |
| *Staphylococcus aureus* Methicillen-resistant (MRSA) | 30 seconds | 99.99% |
| *Escherichia coli* | 30 seconds | 99.99% |
| *Pseudomonas aeruginosa* | 30 seconds | 99.99% |
| *Candida albicans* | 30 seconds | 97.99% |

The invention is in practically non-toxic according to toxicity ratings as documented in *Clinical Toxicology of Commercial Products*, Gleason, Martin H., et al, 1963, and non-toxic by definition in the Federal Hazardous Substances Act (FHSA). The invention exhibits minimal dermal irritation with a 0.08% Draize equivalent in the The Draize Dermal Irritation Test.

Having thus described the invention, what is claimed and desired to be secured by Letters Patent is:

1. A preoperative surgical skin scrub and wound disinfectant comprising:
   an aqueous solution containing a quarternary ammonium compound at approximately 3% by weight;
   a substituted phenolic compound at approximately 3% by weight;
   water at approximately 55% by weight;
   a viscosity builder and emulsifier agent, said viscosity building and emulsifier agent comprising a synthetic phospho lipid, said phospho lipid comprising cocamidopropyl betaine at approximately 3% by weight;
   a detergent, said detergent comprising sodium lauryl sulfate at approximately 21%-23% by weight;
   an emollient, said emollient comprising aloe vera gel at approximately 0.1% to 0.2% by weight;
   a healant, said healant comprising hydrolyzed collagen at about 0.1% to 0.2% by weight;
   a coloring agent, said coloring agent comprising FD&C Yellow No. 10 at approximately 0.0002% by weight; and
   a fragrance.

2. The invention of claim 1 wherein the quaternary ammonium compound further comprises a phosphate imidazolinium compound of the general formula:

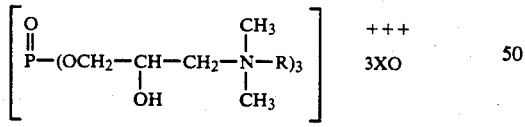

wherein R is a tertiary amine radical of from 6 to 40 carbon atoms; and X is an anion.

3. The invention of claim 1 including a tertiary ammonium compound comprising a phosphate quaternary compound conforming the general formula:

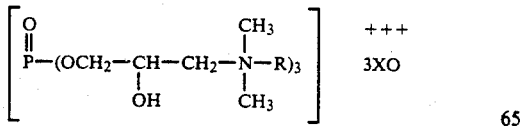

wherein R is a tertiary amine radical of from 6 to 40 carbon atoms and X is an anion.

4. The invention of claim 1 wherein the substituted phenolic compound further comprises chloroxylenol.

5. The invention of claim 1 wherein the substituted phenolic compound further comprises parachlormetaxylenol.

6. The invention of claim 1 wherein the fragrance added further comprises honey and almond extract, approximately 0.24% by weight.

7. A disinfectant to be used on human skin comprising an aqueous solution containing water, at approximately 55% by weight;
   a quantenary ammonium compound, at approximately 3% by weight;
   a substituted phenolic compound, at approximately 3% by weight;
   citric acid at approximately 0.14% by weight;
   cocamidopropyl betaine, at approximately 3% by weight;
   sodium lauryl sulfate, at approximately 22% by weight;
   cocamide DEA, at 8% by weight;
   propylene glycol, at approximately 5% by weight;
   aloe vera gel, at approximately 0.12% by weight;
   hydrolized collagen, at approximately 0.12% by weight;
   fragrance at approximately 0.24% by weight; and
   a coloring agent at approximately 0.0002% by weight.

8. The invention of claim 7 wherein the quaternary ammonium compound further comprises a phosphate imidazolinium compound.

9. The invention of claim 7 wherein the quaternary ammonium compound further comprises a phosphate quaternary compound.

10. The invention of claim 7 wherein the substituted phenolic compound further comprises chloroxylenol.

11. The invention of claim 7 wherein the substituted phenolic compound further comprises parachlormetaxylenol.

12. The invention of claim 7 wherein the coloring agent further comprises FD&C Yellow No. 10.

13. A method for making a preoperative surgical skin scrub and wound disinfectant comprising the steps of:
   measuring out water, an amount approximately 37% of the final formulation by weight;
   heating the water to about 190° F. and maintaining the temperature;
   mixing in order: citric acid approximately 0.14% by weight, cocamidopropyl betaine approximately 3% by weight, a quaternary ammonium compound, approximately 3% by weight, EDTA, approximately 0.05% by weight, sodium lauryl sulfate, approximately 22% by weight, cocamide DEA approximately 8% by weight;
   mixing and adding in order, to the above mixture: propylene glycol, approximately 5% by weight; a substituted phenolic compound, approximately 3% by weight;
   cooling the above mixtures to 120° F.;
   adding, in order, aloe vera gel, approximately 0.12% by weight; hydrolyzed collagen, approximately 0.12% by weight; fragrance, approximately 0.24% by weight;
   adding coloring agent, approximately 0.0002% by weight; and adding water approximately 18.1% by weight of the final compound.

14. The method of claim 13 further comprising controlling the pH of the final mixture adding cocamide DEA to maintain the pH at approximately 5-8.

* * * * *